United States Patent [19]

Williams

[11] Patent Number: 5,746,197
[45] Date of Patent: May 5, 1998

[54] EXTENSION FOR METERED DOSE INHALER

[76] Inventor: Jeffery W. Williams, 7512 Mahaffey Dr., New Port Richey, Fla. 34653

[21] Appl. No.: 517,109

[22] Filed: Aug. 18, 1995

[51] Int. Cl.⁶ .................. A61M 11/00; A61M 15/08; A61M 16/00; A62B 9/06
[52] U.S. Cl. ............... 128/200.23; 128/207.14; 128/203.23
[58] Field of Search .................. 128/200.14, 200.23, 128/200.24, 200.26, 203.12, 203.23, 207.14–207.17, 911, 912, 200.15

[56] References Cited

U.S. PATENT DOCUMENTS

| | | | |
|---|---|---|---|
| 79,015 | 6/1868 | Schulz | 128/200.15 |
| 327,237 | 9/1885 | Clark | 128/200.15 |
| 862,737 | 8/1907 | Hill et al. | 128/200.15 |
| 990,277 | 4/1911 | Lauderdale | 128/200.15 |
| 2,865,370 | 12/1958 | Gattone | |
| 3,001,524 | 9/1961 | Maison et al. | 128/200.23 |
| 3,998,226 | 12/1976 | Harris | 128/203.15 |
| 4,953,545 | 9/1990 | McCarty | |
| 5,012,803 | 5/1991 | Foley et al. | 128/200.23 |
| 5,074,294 | 12/1991 | Chiesi | |
| 5,368,016 | 11/1994 | Henry | |
| 5,507,278 | 4/1996 | Karell | 128/200.23 |

OTHER PUBLICATIONS

Foregger Article, "Disposable Airways", Form #4DD, Dec. 1993, Air Products, Allentown, PA 18105.

*Primary Examiner*—Kimberly L. Asher
*Attorney, Agent, or Firm*—C. Douglas McDonald Jr. & Associates, P.A.

[57] ABSTRACT

An extension that is attachable to metered dose inhalers for more effective and efficient delivery of the medication to the lungs of the user. The extension comprises a member having a bore therethrough that is sized and configured at a first end to match the size and shape of the inhaler nozzle, tapers to a reduced cross-section and extends with a generally uniform cross-section for at least one inch to the second end so as to force the user to slowly inhale the medication into the lungs. An adaptor attached to the first end of the member receives the nozzle therein so that the nozzle is in fluid flow communication with the bore of the member. A portion of the member, including the second end, defines a mouthpiece at least one and one half inches long that is receivable in the mouth of a user.

7 Claims, 2 Drawing Sheets

EXTENSION FOR METERED DOSE INHALER

BACKGROUND OF THE INVENTION

1. Field of the Invention

The present invention relates to metered dose inhalers that deliver a predetermined dose of medication within a user's mouth for subsequent inhalation into the lungs. More particularly, it relates to an extension that delivers the medication to the back of the patient's mouth for more effective delivery of the medication. The extension is particularly useful for the treatment of chronic obstructive pulmonary disease (emphysema and chronic bronchitis).

2. Description of the Prior Art

There are an estimated 15,000,000 Americans that have chronic obstructive pulmonary disease and it was identified as the fifth leading cause of death in 1991. Chronic obstructive pulmonary disease is a term that covers two types of lung disease, emphysema and chronic bronchitis, both of which are caused by smoking and other factors. The effect of both diseases is continuous airway obstruction. Metered dose inhalers are rapidly becoming the most used apparatus for treatment of and relief from these diseases.

Effective treatment of respiratory illnesses and disorders by application of medication directly to the lungs is well known and has resulted in a search for an effective apparatus and method for delivering the medication in the proper dosage. Standard metered dosage inhalers have effectively produced an aerosol of the medication in a predetermined dosage for delivery to the lungs; however, through improper administration technique by the user as well as inefficiencies in the delivery system, frequently less than 10 percent of the medication reaches the user's lungs. Much of the medication coats the interior of the mouth, the tongue, the back of the throat and the trachea, eventually being ingested without benefit to the user. This is due to the wide dispersal of the aerosol mist as the mist enters the mouth of the user, improper breathing by the user or inefficiencies in the inhaler itself. When only a small proportion of the dosage reaches the lungs it is unlikely that a proper dosage is being received by the user. Medication that is deposited in the mouth may lead to oral candidiasis and the medication that is ingested may be responsible for side effects.

Typical metered dose inhalers eject the medication in a short burst of vapor traveling at a relatively high discharge velocity, but it has been shown that a slow and deep inhalation coordinated with activation of the inhaler increases the amount of medication received in the lungs. Much of the prior art has attempted to solve this problem by providing various enlarged chambers that receive the discharge from the inhaler and hold it therein until withdrawn by the user. In particular, U.S. Pat. No. 4,926,852 issued to Zoltan, et al., U.S. Pat. No. 5,203,323 issued to Tritle, U.S. Pat. No. 5,042,467 issued to Foley, and U.S. Pat. No. 4,470,412 issued to Nowacki, et al., are each examples of expansion chambers.

The patent issued to Gattone, U.S. Pat. No. 2,865,370 discloses an apparatus for attachment to a pressurized container for activating that container. This apparatus also has a conical extension that is removable.

Notwithstanding the existence of such prior art, it remains clear that there is a need for a medication delivery device that reduces the amount of medication that is received upon the mouth surfaces, is small and easy to transport and is easy to clean. Such a device would deliver the medication in as close proximity to the lungs as possible without causing discomfort to the user.

SUMMARY OF THE INVENTION

The present invention relates to an extension that is attachable to metered dose inhalers for more effective and efficient delivery of the medication to the lungs of the user. Most simply stated, the extension comprises a member having a first end and a second end and a bore extending therethrough that also has a first end and a second end. The first end of the member is sized and configured for attachment to an inhaler so that the first end of the bore is in fluid flow communication with the inhaler. A portion of the member, including the second end thereof, defines a mouthpiece that is receivable within the mouth of the user. The mouthpiece extends at least one and one half ($1\frac{1}{2}$) inches so that the second end of the member lies proximal to the user's throat. At least a portion of the bore within the mouthpiece has a generally uniform right cross-sectional area that is no greater than 0.12 sq. inches.

The invention, accordingly, comprises an article of manufacture possessing the features, properties, and the relation of elements which will be exemplified in the article hereinafter described, and the scope of the invention will be indicated in the claims.

BRIEF DESCRIPTION OF THE DRAWINGS

For a full understanding of the nature and objects of the invention, reference should be had to the following detailed description taken in connection with the accompanying drawings, in which.

Similar reference characters refer to similar parts throughout the several views of the drawings.

DETAILED DESCRIPTION

Figure 1:
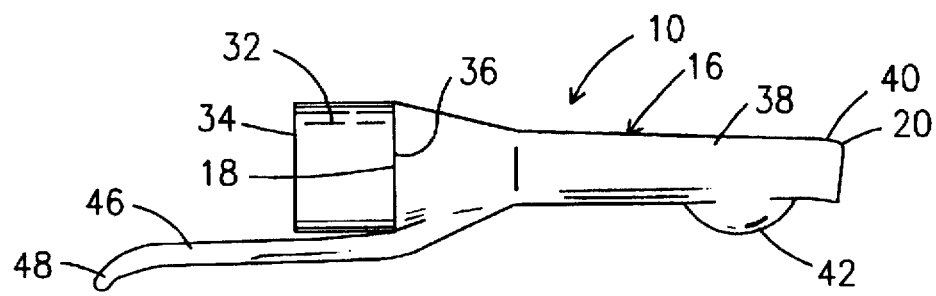
FIG. 1 is a left side elevational view of the extension of the invention.
Figure 2:
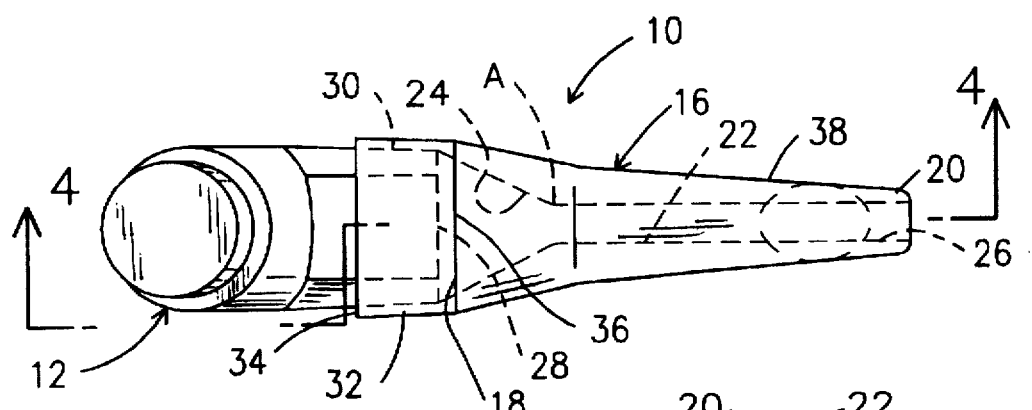
FIG. 2 is a top plan view of the invention of FIG. 1, illustrating the attachment of the extension to a standard metered dose inhaler.
Figure 3:
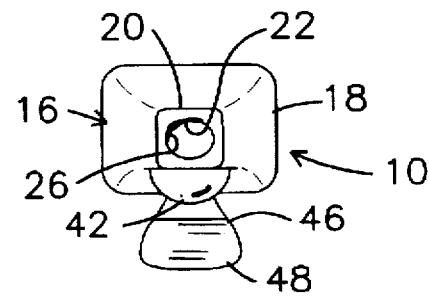
FIG. 3 is a front elevational view of the invention of FIG. 1.
Figure 4:
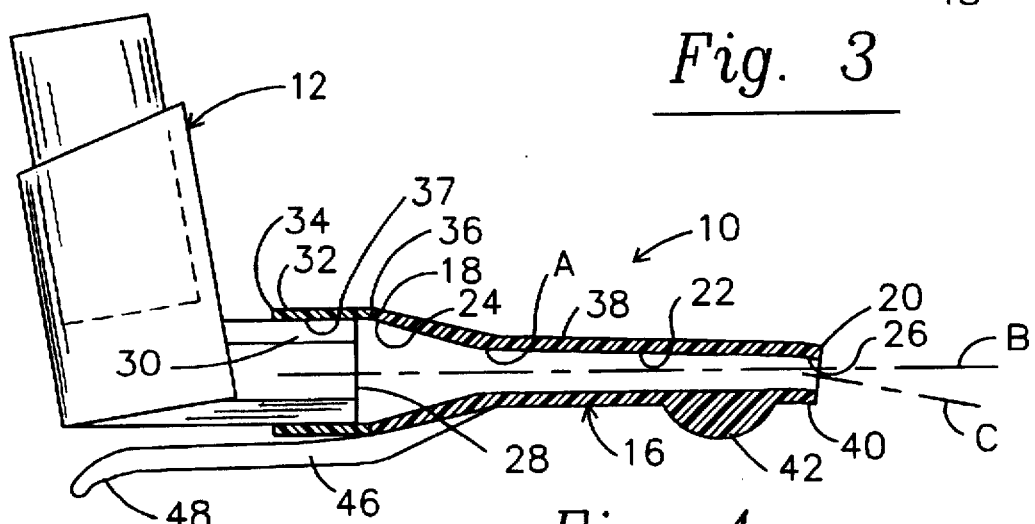
FIG. 4 is a sectional side elevation taken along line 4—4 of FIG. 2.
Figure 5:
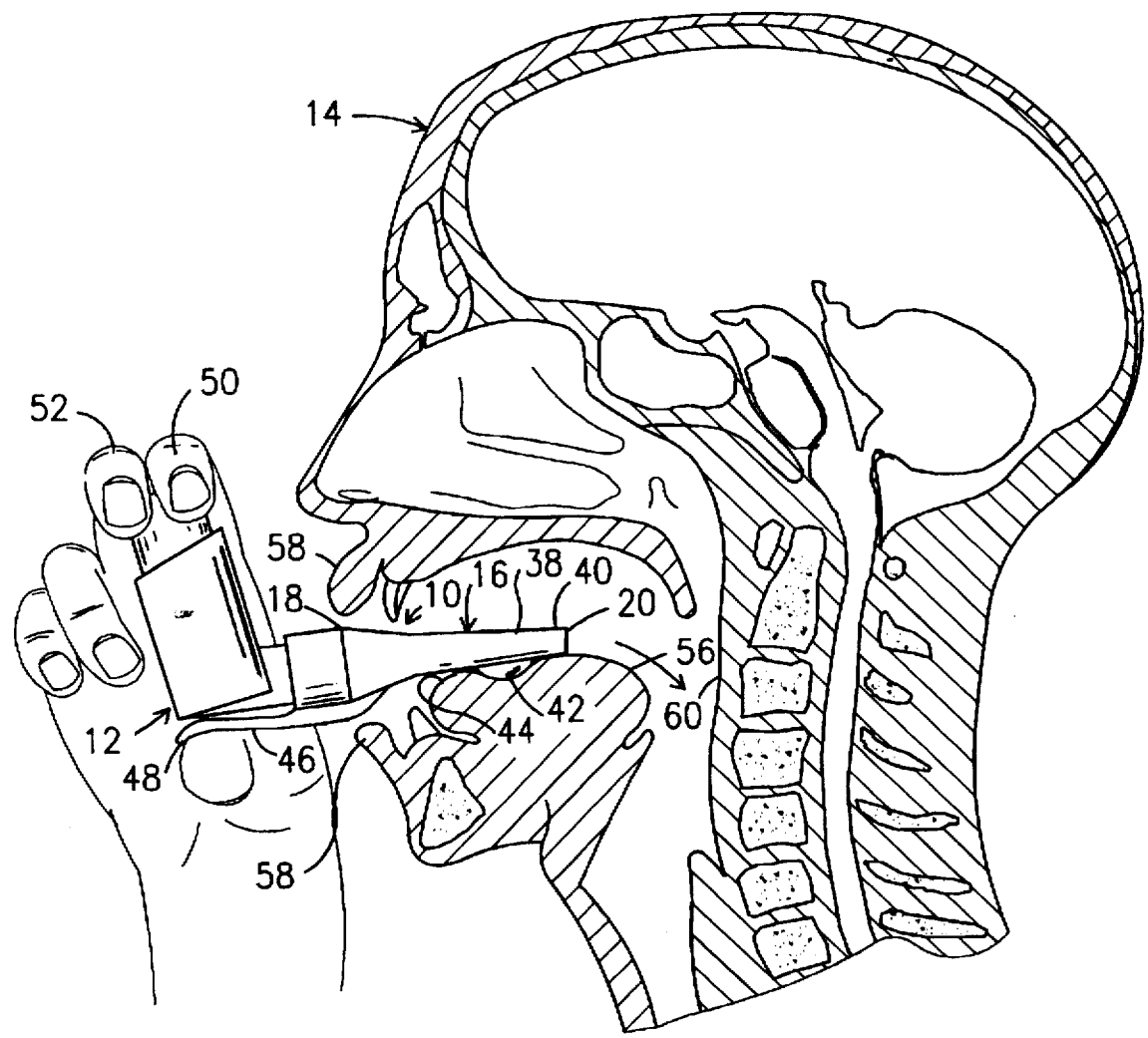
FIG. 5 is a left side elevational view illustrating the extension in use.

A preferred embodiment for the extension of this invention is illustrated in the drawing FIGS. 1-5 and is indicated generally as 10. A representation of a metered dose inhaler is illustrated in FIGS. 2, 4, and 5 and is indicated generally as 12. In FIG. 5, the cross section of a user's head, indicated generally as 14, is shown to more clearly illustrate the positioning of the extension 10 while in use.

Referring first to the view of FIG. 1, it can be seen that the extension 10 is comprised of a member, indicated generally as 16, that has a first end 18 and second end 20. The member 16 has a bore 22 that extends longitudinally from the first end 18 of member 16 to the second end 20 of member 16, defining a first end 24 and a second end 26 of the bore 22. The first end 24 of the bore 22 is sized and configured to have the same general cross-sectional area as the open end 28 of the nozzle 30 of the inhaler 12 so that the vaporized medication readily flows into the bore 22 when the inhaler 12 is activated. In a preferred embodiment, the bore 22 tapers to a reduced cross-sectional area approximately one half (½) inch from the first end of the bore 24 (point A) and extends therefrom to the second end 26 with a generally uniform cross-sectional area. A right cross-section of the bore between point A and second end 26 is generally a circle having an area of 0.05 sq. inches; however, in other embodiments, the bore may be made with other cross-sectional shapes that have a cross-sectional area equal to 0.05 sq. inches. In other preferred embodiments, the cross-sectional area of the bore 22 between the point A and the second end 26 may be within the range of 0.11 sq. inches to and including 0.12 sq. inches and still provide an acceptable result.

An adaptor 32, having a first end 34 and a second end 36, has a passageway 37 therethrough. The second end 36 of the adaptor 32 is attached in fluid flow communication with the first end 18 of the member 16. The first end 34 of the adaptor 32 is sized and configured to receive the nozzle 30 of the inhaler 12 therein. The adaptor 32 is comprised of an elastomeric material that is flexible and conforms to the shape of the nozzles 30 found on most inhalers 12. The adaptor may be comprised of any other flexible material that is suitable for the purpose.

The portion of the member 16 that includes the second end 20 thereof and extends toward the first end 18 for approximately 1½-2 inches is defined as a mouthpiece 38 which is receivable within the mouth of a person 14, as seen in FIG. 5. The longitudinal length of the mouthpiece for use by an adult is approximately two (2) inches and for a child is approximately one and one half (1½) inches.

As best seen in FIGS. 1 and 4, the centerline C of a segment 40 of the mouthpiece 38, that includes the second end 20 of the member 16, angles away from the axis B of the bore 22 as defined by that portion of the bore 22 that is adjacent the first end 24 of the bore 22. As can be seen in FIG. 5, the segment 40 directs the flow of the vaporized medication downwardly into the throat of the person 14.

A projection 42 extends outwardly approximately one-fourth (¼) inch from the member 16 proximal to the second end 20 of the member 16. The projection is formed with smooth rounded contours so that it comfortably engages the tongue 44 of the user 14, as shown in FIG. 5.

A grip element 46 is attached proximal to the first end 18 of member 16 and extends generally longitudinally beyond the first end 18 of member 16. The grip element 46 is generally aligned parallel with axis B and the first end 48 extends under the metered dose inhaler 12, when the inhaler 12 is attached to the extension 10, so that the grip element 46 may be gripped as shown in FIG. 5.

In a preferred embodiment, the extension 10 with the exception of the adaptor 32 is comprised of a generally rigid synthetic resin. While the adaptor 32 is normally flexible, as discussed previously, it may, in other embodiments, be comprised of a rigid synthetic resin and sized and configured to receive the particular shape of the nozzle 30 of a particular metered dose inhaler 12 providing a generally gas tight friction fit.

Having thus set forth a preferred construction for the extension 10 of this invention, it is to be remember that this is but a preferred embodiment. Attention is now invited to a description of the use of the extension 10. The user first selects the appropriate size extension 10, whether for an adult or for a child, and inserts the nozzle 30 within the flexible adaptor 32 to form a generally gas tight fit. The user then grips the metered dose inhaler 12 with the index finger 50 and middle finger 52 so that the thumb 54 may grip the grip element 46 proximal to the first end 48 thereof. The mouthpiece 38 is then inserted within the mouth of the user 14 so that an adult receives approximately two (2) inches of the member 16 therein and a child receives one and one half (1½) inches therein where the mouthpiece does not extend into the throat of the user as shown in FIG. 5. The user 14 then rotates his/her wrist pushing generally downwardly without activating the inhaler 12 so that the tongue 44 is moved out of the way of the second end 26 of the bore 22. The segment 40 of the bore 22 is now generally aligned with the back of the tongue 56 so that the medication issuing from the second end 26 of the bore 22 will not be obstructed.

The user then closes their mouth about the extension 10 so that their lips 58 form a generally air tight seal. The user then activates the inhaler 12 so that a puff of medication issues from the nozzle 30 and is received within the first end 24 of the bore 22. The user inhales generally simultaneously with activation of the inhaler 12. The cross-sectional size of the bore 22 adjacent the second end 26 of the bore 22 restricts the flow of the medication, causing the user 14 to inhale slowly and deeply so that the medication is drawn through the bore 22 in a long smooth breath. The bore 22 directs the mist of medication toward the throat 60 avoiding loss of the medication through contact with and absorption by the interior surfaces of the mouth and tongue 44.

The extension 10 being easily separable from the inhaler 12 and being relatively small and compact, is easily carried on the person or in a purse by the user 14. The extension 10, being made from a synthetic resin and an elastomer is readily cleanable by flushing with anti-bacterial soap and water and by utilizing a flexible cotton tipped applicator to clean the bore 22 as needed.

It will thus be seen that the objects set forth above, among those made apparent from the preceding description, are efficiently attained, and since certain changes may be made in the above article without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall there between.

Now that the invention has been described,

What is claimed is:

1. An extension for metered dose inhalers comprising:
    a member having a first end and a second end and a bore therethrough having a first end and a second end, said first end of said member being sized and configured for attachment to an inhaler so that said bore is in fluid flow communication with the inhaler, said bore tapering to a cross-sectional area no greater than 0.12 square inches and extending with a cross-section of no more than 0.12 inches for at least one inch, a portion of said member, including said second end thereof, defining a mouthpiece at least one and one half inches long, said mouthpiece receivable within the mouth of a user and not extending into the throat of the user.

2. An extension as in claim 1, wherein said bore within said mouthpiece has a right cross-section area in the range of 2 square inches to and including 0.012 square inches.

3. An extension as in claim 1, wherein said bore within said mouthpiece has a right cross-section area of generally 0.05 square inches.

4. An extension as in claim 1 further comprising a grip element attached thereto, said grip element having a first end attached to said member and a second end extending longitudinally outwardly beyond said first end of said extension and generally parallel thereto, such that said second end intersects a longitudinal axis extending through a metered dose inhaler when the metered dose inhaler is attached to said extensions, said second end being configured for gripping by the thumb of a user while the fingers of the user grip the metered dose inhaler when the extension is in use.

5. An extension as in claim 1 wherein said bore has an axis therethrough, and a portion of said axis of said bore adjacent to and including said second end of said bore angles away from the remaining portion of said axis.

6. An extension as in claim 1, wherein said mouthpiece further comprises: a curved projection extending downwardly from said mouthpiece and being formed integrally therewith for engagement with the tongue of the user.

7. An extension as in claim 1 further comprising as adaptor attached to said first end of said member, said adaptor connecting said first end of said member to a metered dose inhaler so that said first end of said bore is in fluid flow communication with the inhaler.

* * * * *

UNITED STATES PATENT AND TRADEMARK OFFICE
CERTIFICATE OF CORRECTION

PATENT NO. : 5,746,197
DATED : May 5, 1998
INVENTOR(S) : Jeffery W. Williams

It is certified that error appears in the above-identified patent and that said Letters Patent is hereby corrected as shown below:

Column 4, line 62, delete "2" and insert therefore -- 0.11

Column 5, line 6, delete "extensions" and insert therefore -- extension

Column 6, line 5, delete "comprising as" and insert therefore -- comprising an --

Signed and Sealed this

Thirtieth Day of June, 1998

Attest:

BRUCE LEHMAN

Attesting Officer

Commissioner of Patents and Trademarks